United States Patent [19]

Fitchmun

[11] Patent Number: 5,760,179

[45] Date of Patent: Jun. 2, 1998

[54] PURIFICATION OF SOLUBLE LAMININ 5

[75] Inventor: Mark Fitchmun, San Diego, Calif.

[73] Assignee: Desmos, Inc., San Diego, Calif.

[21] Appl. No.: 660,841

[22] Filed: Jun. 10, 1996

[51] Int. Cl.$^6$ .............................. C07K 1/00; C12N 5/00
[52] U.S. Cl. .................... 530/350; 530/414; 530/416; 530/417; 530/418; 530/427; 435/240.1; 435/240.2; 435/240.21; 435/240.243
[58] Field of Search ...................... 530/350, 414, 530/416, 417, 418, 427; 435/240.1, 240.2, 240.21, 240.243

[56] References Cited

U.S. PATENT DOCUMENTS

| | | | |
|---|---|---|---|
| 5,422,264 | 6/1995 | Quaranata et al. | 435/240.2 |
| 5,510,263 | 4/1996 | Quaranta et al. | 435/240.243 |
| 5,541,106 | 7/1996 | Jones | 435/240.243 |

FOREIGN PATENT DOCUMENTS

| | | |
|---|---|---|
| WO 92/17498 | 10/1992 | WIPO. |
| WO 94/05316 | 3/1994 | WIPO. |
| WO 95/06660 | 3/1995 | WIPO. |
| WO 95/29187 | 11/1995 | WIPO. |

OTHER PUBLICATIONS

Baker et al, *Experimental Cell Research*, vol. 228, No. 2, pp. 262–270, Feb. 7, 1996.

Miyazaki et al, *Proc. Natl. Acad. Sci, USA*, vol. 90, pp. 11767–11771, 1993.

Rousselle et al, *The Journal of Biological Chemistry*, vol. 270, No. 23, pp. 13766–13770, Jun. 9, 1995.

Chan et al, *J. Invest. Dermatol.*, vol. 105, pp. 75–79, 1995.

W.G. Carter, et al. (1991) "Epiligrin, A New Cell Adhesion Ligand for Integrin α3α1 in Epithelial Basement Membranes", *Cell*, 65:599–610.

B. Hsi, et al. (1987) "Monoclonal Antibody GB$_3$6 Raised Against Human Trophoblast Recognizes a Novel Epithelial Antigen", *Placenta*, 8:209–217.

K. Izumi, et al. (1981) "In Vitro Induction of Ornithine Decarboxylase in Urinary Bladder Carcinoma Cells", *Cancer Research*, 41:405–409.

K. Miyazaki, et al. (1993) "A Large Cell–Adhesive Scatter Factor Secreted by Human Gastric Carcinoma Cells", *Proc. Natl. Acad. Sci. USA*, 90:11767–11771.

P. Rousselle, et al. (1991) "Kalinin: An Epithelium–Specific Basement Membrane Adhesion Molecule That is a Component of Anchoring Filaments", *Journal of Cell Biology*, 114(3):567–576.

H.D. Soule, et al. (1990) "Isolation and Characterization of a Spontaneously Immortalized Human Breast Epithelial Cell Line, MCF–10", *Cancer Research*, 50:6075–6086.

L.A. Staehelin (1974) "Structure and Function of Intercellular Junctions", *Department of Molecular, Cellular and Developmental Biology*, University of Colorado, Boulder, Colorado, pp. 191–283.

L. Tait, et al. (1990) "Ultrastructural and Immunocytochemical Characterization of an Immortalized Human Breast Epithelial Cell Line, MCF–10", *Cancer Research*, 50:6087–6094.

P. Verrando, et al. (1988) "The New Basement Membrane Antigen Recognized by the Monoclonal Antibody GB3 is a Large Size Glycorprotein: Modulation of its Expression by Retinoic Acid", *Biochimica et Biophysica Acta*, 942:45–56.

*Primary Examiner*—Cecilia J. Tsang
*Assistant Examiner*—Abdel A. Mohamed
*Attorney, Agent, or Firm*—Knobbe, Martens, Olson & Bear LLP

[57] ABSTRACT

A method for purifying soluble laminin 5 from conditioned cell culture medium. A nonionic or anionic detergent is added to conditioned medium to a final concentration of between 0.1% and 1.0%. The conditioned medium is purified by cation exchange chromatography and anion exchange chromatography, yielding laminin 5 of at least about 70% purity.

12 Claims, No Drawings

1

PURIFICATION OF SOLUBLE LAMININ 5

FIELD OF THE INVENTION

The present invention relates to purification of a soluble matrix protein. More specifically, the invention relates to purification of the hemidesmosome formation-inducing soluble matrix secreted by certain epithelial cell lines.

BACKGROUND OF THE INVENTION

In vivo, many epithelial cells interact with the underlying extracellular matrix, a network of proteins to which cells attach, via a junction called the hemidesmosome (Staehelin, *Structure and function of Intercellular Junctions*, Department of Molecular, Cellular and Developmental Biology, University of Colorado, Boulder, Colo., pp. 191–283, 1974). The hemidesmosome with its associated structures, including intermediate filaments and anchoring fibrils, forms an adhesion complex. Disruptions of the epithelial-connective tissue interaction are often accompanied by disruption of the hemidesmosome complex. For example, in certain blistering skin diseases such as junctional epidermolysis bullosa, in which epithelial cell-connective tissue interaction is abnormal, it has been proposed that there is biochemical modification in, or loss of, a basement membrane zone-associated component of the hemidesmosome.

Most epithelial cells do not assemble bona fide hemidesmosomes when cultured in vitro, despite the fact that they appear to express all of the necessary adhesion plaque components. Hemidesmosome formation is a major advantage, as cells capable of doing so grow in a more organized, tissue-like fashion than cells unable to form hemidesmosomes. Hemidesmosome formation also enhances the attachment of cells to a substrate. The 804G and NBT II rat bladder carcinoma cell lines are capable of assembling hemidesmosomes in vitro under standard culture conditions. 804G cells produce both an insoluble (deposited onto a substrate) and soluble (secreted into the culture medium) extracellular matrix which induce the formation of hemidesmosomes in unrelated epithelial cells cultured in contact with the matrices. The insoluble and soluble extracellular matrices are described in U.S. Pat. No. 5,541,106 and 5,422,264, respectively the entire contents of which are hereby incorporated by reference. The 804G soluble matrix may be used to coat shaped articles and implantable prosthesis for use both in vivo and ex vivo. U.S. Pat. No. 5,510,263, the entire contents of which are hereby incorporated by reference, discloses the enhanced growth of pancreatic islet cells on the extracellular matrix produced by 804G cells.

Human cell matrix molecules structurally similar to the 804G matrix have also been described. Rouselle et al. (*J. Cell Biol.*, 114:567–576, 1991) and Burgeson et al. (PCT WO92/17498; PCT WO94/05316) describe a molecule called kalinin which is secreted into the culture medium by human keratinocytes and enhances cell attachment. Carter et al. (*Cell*, 65:599–610, 1991; PCT WO95/06660) describe an epithelial ligand complex called epiligrin found in the extracellular matrix of human keratinocytes. In addition, a basement membrane glycoprotein secreted into the culture medium of human keratinocytes (BM600) (Verrando et al., *Biochim. Biophys. Acta*, 942:45–56, 1988; Hsi et al., *Placenta* 8:209–217, 1987) is structurally similar to 804G matrix protein. The human mammary epithelial cell line MCF 10A, available from ATCC (ATCC CRL 10317), also secretes an extracellular matrix molecule into the culture medium which is similar to 804G matrix. This cell line is described by Soule et al. (*Cancer Res.*, 50:6075–6086, 1990) and Tait et al. (*Cancer Res*, 50:6087–6094, 1991).

Purification of the soluble matrix secreted by 804G cells grown in serum-free medium is described in U.S. application Ser. No. 5,422,264. However, there is a need for a scalable process capable of producing product having a high degree of purity. Miyazaki et al. (*Proc. Natl. Acad. Sci. U.S.A.*, 90:11767–11771, 1993) disclose the purification of a ladsin, a protein secreted into the culture medium by STKM-1 human gastric carcinoma cells. The protein was purified from conditioned medium using ammonium sulfate precipitation, gel filtration chromatography, affinity chromatography and anion exchange chromatography.

Thus, there is a need for a large scale purification method which will result in substantially pure laminin 5.

SUMMARY OF THE INVENTION

One embodiment of the present invention is a method of purifying soluble laminin 5 from conditioned medium, comprising the following steps:

(a) adding a nonionic or anionic detergent to said conditioned medium to a final concentration of between about 0.1% and 1.0%;

(b) applying the conditioned medium to a cation exchange column;

(c) applying a gradient of increasing ionic strength or pH to the cation exchange column to elute laminin 5 therefrom;

(d) applying the eluted laminin 5 from step (c) to an anion exchange column; and (e) applying a gradient of increasing ionic strength or decreasing pH to said anion exchange column to elute laminin 5 therefrom, said laminin 5 having a purity of at least about 70%.

Preferably, the conditioned medium is 804G conditioned medium; more preferably, the conditioned medium is MCF 10A conditioned medium. Advantageously, the adjusting step comprises buffer exchange. In one aspect of this preferred embodiment, the buffer exchange step comprises gel filtration chromatography. Advantageously, the buffer is phosphate. According to one aspect of this preferred embodiment, the nonionic detergent is TWEEN-20™. According to another aspect of this preferred embodiment, the cation exchange chromatography is performed with Macro Prep High S. Preferably, the gradient of step (c) is a step gradient of about 200 mM and about 400 mM phosphate, a portion of the laminin 5 eluting at about 400 mM phosphate. In another aspect of the invention, the anion exchange chromatography is performed with Macro Prep High Q. Advantageously, the gradient of step (e) is about 80 mM, 90 mM, 120 mM and 330 mM, a portion of the laminin 5 eluting at about 120 mM. The method may further comprise hydroxyapatite chromatography of the laminin 5 obtained from the anion exchange column.

The present invention also provides isolated secreted laminin 5 of at least about 90% purity as determined by SDS-PAGE.

DETAILED DESCRIPTION OF THE PREFERRED EMBODIMENTS

The present invention provides a method for purifying 804G soluble matrix from conditioned medium (CM) to at least about 90% purity as determined by SDS-PAGE. The 804G cell line is described by Izumi, et al., *Cancer Res.* (1981); 41:405–409, and is maintained as a Budapest Treaty patent deposit with the American Type Culture Collection (ATCC), Rockville, Md., under accession number ATCC 11555, made Feb. 24, 1994. All restrictions upon availability to the public of these cell lines will be irrevocably removed upon issuance of a patent. 804G cells are cultured in Dulbecco's Modified Eagle's Medium (DMEM) containing 10% fetal bovine serum (FBS) and 2 mM glutamine.

All of the aforementioned matrix molecules are structurally and functionally related to laminin 5 proteins. Accordingly, although the purification of soluble laminin 5 from 804G CM is described herein, this procedure may also be used to purify laminin 5 from conditioned media of any desired cell type, including human keratinocytes and MCF 10A human epithelial cells.

Adjustment of buffer composition prior to purification

Prior to the first laminin 5 purification step, 804G CM or other source of laminin 5 is preferably mixed with one or more buffer salts capable of providing adequate buffering capacity between pH values of about 6.0 and 10. Suitable buffer systems for use in this step include phosphate, Tris-HCl, borate, (N-tris[Hydroxymethyl]methyl-2-aminoethane sulfonic acid) (TES), (Piperazine-N,N'-bis[2-ethanesulfonic acid]) (PIPES), (N-[2-Hydroxyethyl]piperazine-N'-[2-ethanesulfonic acid]) (HEPES), (N-tris[Hydroxymethyl] methyl-glycine) (TRICINE), (3-[N-Morpholino] propane sulfonic acid) (MOPS) and other buffers known to one of ordinary skill in the art. These buffers are all available from Sigma Chemical Co., St. Louis, Mo.

The composition of CM is optionally adjusted by addition of one or more buffer salts. In a preferred embodiment, the adjusted conditioned medium has an ionic strength of between about 10 mM and about 300 mM, preferably about 100 mM. In a particularly preferred embodiment, a nonionic or anionic detergent is added to the conditioned medium to a final concentration of between about 0.01% and about 1.0%. In a particularly preferred embodiment, the detergent concentration is about 0.2%. Suitable nonionic detergents include digitonin, polyoxyethylene ethers of the Brij™ series (i.e. 2 cetyl ether, 10 cetyl ether), polyoxyethylenesorbitan esters (TWEEN™ series; i.e. polyoxyethylenesorbitan monolaurate (TWEEN-20™), polyoxyethylenesorbitan monooleate (TWEEN-80™), (octylphenoxy)-polyoxyethanol (NONIDET-P40™), t-octylphenoxypolyethoxyethanol (TRITON X-100™), glucamides and octylglucosides. Anionic detergents contemplated for use in the invention include caprylic acid, cholic acid, deoxycholic acid, 1-decanesulfonic acid, N-lauroylsarcosine and lauryl sulfate. All of the aforementioned detergents are available from Sigma Chemical Co., St. Louis, Mo.

In another preferred embodiment, the CM contains a divalent cation-chelating agent in an amount from about 1.0 mM to about 10 mM, although the preferred chelating agent is EDTA, other chelating agents (i.e. EGTA) known to one of ordinary skill in the art are also within the scope of the invention. The EDTA chelates divalent cations, eliminating undesirable metalloproteinase activity, as well as other undesirable divalent cation-dependent processes.

Increasing the pH by least about 0.3 units, adding detergent to at least about 0.1% (v/v), and increasing the salt concentration by about 50 mM improves laminin 5 recovery during the subsequent buffer exchange step. Each of these parameters operates independently to improve the purification procedure. The process described herein therefore includes one, two or all of these elements. The slightly alkaline pH also reduces the proteolytic activity of lysosomal enzymes present in conditioned media. The adjusted CM is stored at −80° C. awaiting purification.

The conditioned medium which has been adjusted to the conditions described above may be directly applied to a cation exchange column or may be buffer exchanged. Buffer exchange allows processing of large quantities of CM in several hours and removes undesirable substances from conditioned medium which would hinder further purification steps. CM is thawed and applied to a gel filtration column equilibrated with the desired buffer. Although cross-linked dextran beads having a bead diameter of 20–80 μM (SEPHADEX G-25™) gel filtration matrix (Pharmacia, Piscataway, N.J.) was used in the buffer exchange step described herein, other conventional gel filtration materials known to one of ordinary skill in the art may also be used including Biogel P6 (Bio-Rad Laboratories, Richmond, Calif.) and cross-linked dextran beads having a bead diameter of 20–80 μM. Other buffer exchange methods including dialysis and diafiltration (ultrafiltration), techniques well known to one of ordinary skill in the art, are also within the scope of the present invention.

One major advantage of the buffer exchange step is the removal of substances present in CM which could negatively impact the behavior of chromatography columns used in subsequent purification steps. The presence of detergent during buffer exchange improves the recovery of laminin 5 and the resolving power of the subsequent cation exchange step. The ionic concentration of about 100 mM and a neutral or slightly alkaline pH prevent the bulk of protein present in CM from interacting with the subsequent cation exchange column; however, these conditions promote the adsorption of laminin 5 to the cation exchange resin. The presence of EDTA or other suitable chelating agents ensures the removal of divalent cations.

Cation exchange chromatography

The adjusted conditioned medium is then applied to a cation exchange column equilibrated with the same buffer previously used. Many cation exchange matrices are suitable for use in the present invention, including Macro Prep High S (Bio-Rad) and SP Sepharose fast flow (Pharmacia). Protein fractions containing laminin 5 are eluted with a step gradient of about 200 mM (peak 1) and about 400 mM (peak 2) phosphate, as well as with 1M NaOH (peak 3). The use of other salts for elution of laminin 5, including KCl and NaCl, for example, is also contemplated, as is the use of a continuous salt gradient. In addition, because gradients of increasing pH are also known to elute proteins from cation exchange columns, the use of such a gradient is also contemplated. During cation exchange chromatography, the EDTA is completely removed to prevent negative effects on the anion exchange procedure which follows. Although laminin 5 is eluted in three peaks, the portion of laminin 5 eluted in peak 2 is further purified by anion exchange chromatography. The buffers used during this fractionation contain only two ionic species, a cation and an anion, which simplifies and expedites the following anion exchange chromatography because additional small anions interact with, and differentially effect, the behavior of anion exchange resins with respect to protein adsorption and desorption. The detergent ensures good protein separation and recovery of laminin 5, possibly by preventing protein aggregation, thereby reducing the apparent charge heterogeneity of laminin 5.

Anion exchange chromatography

The material collected from peak 2 of the cation exchange column is applied to an anion exchange column equilibrated with an ionic concentration of 80 mM at a pH of about 7.0 containing about 0.05% nonionic or anionic detergent. Many anion exchange matrices are suitable for use in the present invention, including Macro Prep High Q (Bio-Rad) and Q Sepharose fast flow (Pharmacia). The bound protein is eluted with a salt step gradient of about 80 mM (peak 1), 90 mM (peak 2), 120 mM (peak 3) and 330 mM (peak 4) phosphate. The use of other salts for elution of laminin 5, including KCl and NaCl, for example, is also contemplated, as is the use of a continuous salt gradient. In addition, because gradients of decreasing pH are also known to elute proteins from anion exchange columns, the use of such a gradient is also contemplated. The laminin 5 in peak 3 is at least about 70% pure as determined by sodium dodecyl sulfate polyacrylamide gel electrophoresis (SDS-PAGE) on a 4–20% gradient gel and visualization of three major protein bands of about 135 kDa, 140 kDa and 150 kDa by Coomassie Blue staining.

During the anion exchange step, the detergent concentration is reduced because it does not play as critical a role in protein separation and laminin 5 recovery as it does in earlier steps. Most of the contaminants which co-elute with laminin 5 from the preceding cation exchange step do not co-elute with laminin 5 during this procedure. The buffers used during this procedure contain only two ionic species, a cation and an anion which simplifies and expedites the anion exchange chromatography because different small anions may interact with, and differentially effect, the behavior of anion exchangers with respect to protein absorption and desorption.

Hydroxyapatite chromatography

Material collected in peak 3 from the anion exchange column is optionally applied to a hydroxyapatite column equilibrated with about 100 mM phosphate, at a pH of about 7.7. Laminin 5 of at least about 90% purity as determined by SDS-PAGE is eluted from the column with about 300 mM sodium phosphate. The purity of the material is assessed by SDS-PAGE.

The purification procedure for laminin 5 is described in detail in the following examples.

EXAMPLE 1

Preformulation of 804G CM 804G rat bladder carcinoma cells were grown past confluence in DMEM supplemented with 10% FBS and 2 mM glutamine. The 804G cell line is described by Izumi et al., *Cancer Res.*, (1981) 41:405–409, and was deposited with the American Type Culture Collection, 12301 Parklawn Drive, Rockville, Md., on Feb.24, 1994, and assigned accession number ATCC CRL 11555. All restrictions on the availability to the public of the deposited cells will be irrevocably removed upon the granting of a patent. Four parts of conditioned medium were mixed with one part 500 mM sodium phosphate, pH 7.7, 15 mM EDTA, 1.0% TWEEN-20. The diluted CM was stored at −80° C. awaiting purification.

Preformulated CM was buffer exchanged as described in the following example.

EXAMPLE 2

Buffer Exchange

Approximately 20 liters of preformulated 804G CM prepared as described in Example 1 were thawed and buffer exchanged into 100 mM sodium phosphate, pH 7.0, 3 mM EDTA, 0.2% TWEEN-20™, via gel permeation chromatography on a SEPHADEX G-25™ column (Pharmacia). The column measured 9.0 cm in diameter and 60 cm in length. The bed volume was 4.0 liters. The entire procedure was performed at 10° C. with a flow rate of 100 ml/min. The column was equilibrated in 100 mM sodium phosphate, pH 7.0, 3 mM EDTA, 0.2% TWEEN-20™. One liter of preformulated 804G CM was pumped into the column, followed by 8.0 liters of 100 mM sodium phosphate, pH 7.0, 3 mM EDTA, 0.2% TWEEN-20™. One liter fractions were collected and monitored for protein content by absorbance at 280 nm, starting about three minutes after the addition of the 8.0 liters of buffer, and ending about 10 minutes later. The pumping steps were repeated until all of the CM has been exchanged into 100 mM sodium phosphate, pH 7.0, 3 mM EDTA, 0.2% TWEEN-20™. The column was regenerated and stored in 100 mM NaOH.

The buffer exchange step circumvents the need to dialyze the material using conventional dialysis bags, a time-consuming process. Using the buffer exchange method, 20 liters of medium may be dialyzed in several hours rather than several days.

The buffer exchanged CM was then fractionated by cation exchange chromatography as described in the following example.

EXAMPLE 3

Cation Exchange Chromatography

A 2.6 cm diameter×24 cm length column having a volume of 125 ml was packed with Macro Prep High S cation exchange resin (Bio-Rad). The entire procedure was performed at 10° C. at a flow rate of 14 ml/min except where indicated. The column was equilibrated with 100 mM sodium phosphate, pH 7.0, 0.2% TWEEN20™, 3 mM EDTA which had been cooled to 10° C. Approximately 20 liters of buffer-exchanged CM prepared according to Example 2 was pumped through the column, followed by pumping 100 mM sodium phosphate, pH 7.0, 0.2% TWEEN-20™ for 30 minutes. 200 mM sodium phosphate, pH 7.4, 0.2% TWEEN-20™, maintained at 20° C.–25° C. was then pumped through the column for 36 minutes. Starting five minutes after this step, and lasting for 35 minutes, a protein fraction containing laminin 5 as determined by SDS-PAGE (volume of about 490 ml) was eluted from the column and stored at −20° C. 400 mM sodium phosphate, pH 7.4, 0.2% TWEEN-20™, maintained at 20° C.–25° C., was then pumped through the column for 40 minutes and a single protein peak containing laminin 5 (volume of about 210 ml) was eluted from the column and stored at −20° C. Protein remaining on the column was eluted with 1.0M NaOH and the column was regenerated and stored in 100 mM sodium phosphate, pH 7.0, 0.1% sodium azide.

The laminin 5 recovered from the cation exchange column was further purified by anion exchange chromatography as described below.

EXAMPLE 4

Anion Exchange Chromatography

The cation exchanged material which eluted with 400 mM sodium phosphate from Example 3 was fractionated by anion exchange chromatography using a Macro-Prep High Q Support (Bio-Rad laboratories). The column dimensions were 2.6 cm diameter×15 cm in length. The column volume was 80 ml. The entire procedure was performed at room temperature at a flow rate of 2.0 ml/min.

The column was washed for three hours with 1.0M NaOH, then equilibrated for seven hours with 80 mM sodium phosphate, pH 7.0, 0.04% TWEEN-20™. The cation exchanged material was thawed, diluted with four parts ultrapure water and pumped through the column. 80 mM sodium phosphate, pH 7.0, 0.04% TWEEN-20™ (140 ml) was then pumped through the column for 70 minutes, followed by pumping of 90 mM sodium phosphate, pH 7.0, 0.04% TWEEN-20™ (250 ml) for 125 minutes. During this step, an eluted protein fraction was discarded. 120 mM sodium phosphate, pH 7.0, 0.04% TWEEN-20™ was then pumped through the column for 90 minutes. A protein fraction containing laminin 5 started eluting about 30 minutes after the beginning of this step and was collected for 75 minutes, resulting in a fraction volume of 150 ml which was stored at −20° C. This fraction contained laminin 5 having a purity of at least about 70% as determined by SDS-PAGE. Protein remaining on the column was eluted with 330 mM sodium phosphate, pH 7.0 for 50 minutes, then with 20% ethanol, 20% acetic acid. The column was stored in 20% ethanol containing 50 mM sodium phosphate, pH 7.0.

The anion exchanged material was subjected to a final purification step on hydroxyapatite as described in the following example.

EXAMPLE 5

Hydroxyapatite Chromatography

Material eluted with 120 mM sodium phosphate described in Example 4 was thawed, diluted 8:3 with ultrapure water (8 parts sample to 3 parts water), and pumped over a Macro-Prep Ceramic Hydroxyapatite column (Bio-Rad Laboratories) having a diameter of 1.6 cm, a length of 7.5 cm and a volume of 15 ml. The procedure was performed at room temperature with a flow rate of 1.0 ml/min. The column was equilibrated with 100 mM sodium phosphate, pH 7.7, 0.0025% TWEEN-20™. The 8:3 diluted material was then pumped through the column. 100 mM sodium phosphate, pH 7.7 was pumped over the column for 45 minutes, followed by 100 mM sodium phosphate, pH 7.7, 0.0025% TWEEN-20™ for 45 minutes. 300 mM sodium phosphate, pH 7.7, 0.0025% TWEEN-20™ (30 ml) was then pumped over the column for 30 minutes. Laminin 5 of at least about 90% purity, as assessed by SDS-PAGE, eluted from the column in a single peak containing approximately 2.5 mg protein in a volume of about 8 ml. 700 mM sodium phosphate, pH 7.7, 0.0025% TWEEN-20™ was then pumped over the column for 38 minutes, followed by 1M NaOH and PBS, pH 7.4, 0.1% sodium azide. The column was stored in PBS, pH 7.4, 0.1% sodium azide.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of purifying soluble laminin 5 from conditioned medium, comprising the following steps:
   (a) adding a nonionic or anionic detergent to said conditioned medium to a final concentration of between about 0.01% and 1.0%;
   (b) applying said conditioned medium to a cation exchange column;
   (c) applying a gradient of increasing ionic strength or pH to said cation exchange column to elute laminin 5 therefrom;
   (d) applying the eluted laminin 5 from step (c) to an anion exchange column; and
   (e) applying a gradient of increasing ionic strength or decreasing pH to said anion exchange column to elute laminin 5 therefrom, said laminin 5 having a purity of at least 70%.

2. The method of claim 1, wherein said conditioned medium is 804G conditioned medium.

3. The method of claim 1, wherein said conditioned medium is MCF 10A conditioned medium.

4. The method of claim 1, wherein said nonionic detergent is polyoxyethylenesorbitan monolaurate.

5. The method of claim 1, wherein said cation exchange chromatography is performed with Macro Prep High S ion exchange resin.

6. The method of claim 1, wherein the gradient of increasing ionic strength or pH of step (c) is a step gradient of about 100 mM, 200 mM and about 400 mM phosphate, a portion of said laminin 5 eluting at about 400 mM phosphate.

7. The method of claim 1, wherein said anion exchange chromatography is performed with Macro Prep High Q ion exchange resin.

8. The method of claim 1, of step (e) is a step wherein the gradient of increasing ionic strength or decreasing pH gradient of about 80 mM, 90 mM, 120 mM and 330 mM phosphate, a portion of said laminin 5 eluting at about 120 mM.

9. The method of claim 1, further comprising hydroxyapatite chromatography of the laminin 5 obtained from step (e).

10. The method of claim 1, further comprising buffer exchange of said conditioned medium prior to step (a).

11. The method of claim 10, wherein said buffer exchange comprises gel filtration chromatography.

12. The method of claim 10, wherein said buffer is phosphate.

* * * * *

UNITED STATES PATENT AND TRADEMARK OFFICE
CERTIFICATE OF CORRECTION

PATENT NO. : 5,760,179

DATED : June 2, 1998

INVENTOR(S) : Mark Fitchmun

It is certified that error appears in the above-identified patent and that said Letters Patent is hereby corrected as shown below:

```
     Column 3, line 52, please replace "10 mM. although" with --10 mM,
although--.
     Column 6, line 32, please replace "TWEEN20™" with --TWEEN-20™--.
     Column 8, line 38, please delete "of step (e) is a step".
     Column 8, line 39, between "pH" and "gra-", please insert --of step
(e) is a step--.
```

Signed and Sealed this

Seventeenth Day of November, 1998

Attest:

BRUCE LEHMAN

Attesting Officer

Commissioner of Patents and Trademarks